(12) United States Patent
Qian et al.

(10) Patent No.: US 8,412,541 B2
(45) Date of Patent: Apr. 2, 2013

(54) METHOD AND SYSTEM FOR INTELLIGENT QUALITATIVE AND QUANTITATIVE ANALYSIS FOR MEDICAL DIAGNOSIS

(75) Inventors: Jianzhong Qian, Princeton Junction, NJ (US); Guo-Qing Wei, Plainsboro, NJ (US); Li Fan, Belle Mead, NJ (US)

(73) Assignee: Edda Technology, Inc., Princeton Junction, NJ (US)

( * ) Notice: Subject to any disclaimer, the term of this patent is extended or adjusted under 35 U.S.C. 154(b) by 1653 days.

(21) Appl. No.: 10/916,431

(22) Filed: Aug. 12, 2004

(65) Prior Publication Data
US 2005/0038678 A1  Feb. 17, 2005

Related U.S. Application Data

(60) Provisional application No. 60/494,802, filed on Aug. 14, 2003.

(51) Int. Cl.
*G06Q 50/00* (2012.01)
(52) U.S. Cl. ............. 705/3; 707/600; 707/603; 715/971
(58) Field of Classification Search .................. 705/2–4; 715/971; 707/600, 603
See application file for complete search history.

(56) References Cited

U.S. PATENT DOCUMENTS

| | | | |
|---|---|---|---|
| 5,473,537 A | 12/1995 | Glazer et al. | |
| 5,692,501 A | 12/1997 | Minturn | |
| 5,937,387 A | 8/1999 | Summerell et al. | |
| 6,021,404 A * | 2/2000 | Moukheibir | 706/46 |
| 6,058,322 A * | 5/2000 | Nishikawa et al. | 600/408 |
| 6,248,063 B1 * | 6/2001 | Barnhill et al. | 600/300 |
| 6,322,504 B1 | 11/2001 | Kirshner | |
| 6,334,192 B1 | 12/2001 | Karpf | |
| 6,601,055 B1 | 7/2003 | Roberts | |
| 7,191,183 B1 * | 3/2007 | Goldstein | 707/602 |
| 7,392,199 B2 * | 6/2008 | Karlov et al. | 705/2 |
| 2004/0122703 A1 * | 6/2004 | Walker et al. | 705/2 |

FOREIGN PATENT DOCUMENTS
WO  WO 03/040987  5/2003

OTHER PUBLICATIONS

Zeffane, R. M., & Cheek, B. (1994). The use of different information channels in an organizational context. Management Research News, 17(3), 1-1. Retrieved from http://search.proquest.com/docview/223526345?accountid=14753.*
European Search Report issued in European Patent Application No. EP 04 78 1226, mailed Feb. 3, 2009.
Qian, J., "Intelligent Diagnostic Imaging and Analysis", Frontiers in Biomedical Engineering, 1st Annual World Congress of Chinese Biomedical Engineers, Dec. 2002, pp. 315-325.
Wang, X-H., et al., "Computer-assisted diagnosis of breast cancer using a data-driven Bayesian belief network", International Journal of Medical Informatics, May 1999, pp. 115-126, vol. 54 No. 2, Elsevier Scientific Publishers.
Ezquerra, N., et al., "Interactive, knowledge-guided visualization of 3D medical imagery", Future Generations Computer Systems, Feb. 1999, pp. 59-73, vol. 15 No. 1, Elsevier Science Publishers, Amsterdam NL.

(Continued)

*Primary Examiner* — Gerald J. O'Connor
*Assistant Examiner* — Mark Holcomb
(74) *Attorney, Agent, or Firm* — SNR Denton US LLP

(57) ABSTRACT

An Intelligent Qualitative and Quantitative Analysis (IQQA) system and method is disclosed that allows a user to specify certain identifying information used to search and obtain medically-related information from different sources. The medically-related information may be of different types and may be dynamically fused, when needed, to generate matrices of diagnostic information. Medical decisions such as a diagnostic decision may be made based on such matrices of diagnostic information.

61 Claims, 8 Drawing Sheets

OTHER PUBLICATIONS

Chiou, Y.S. P., et al., "Neural-Knowledge Base Object Detection in Hybrid Lung Nodule Detection (HLND) System", Neural Networks, IEEE World Congress on Computational Intelligence, 1994, pp. 4180-4185.

Taylor, P., et al., "Computer Aids for Decision-Making in Radiology", Feb. 1996.

International Search Report issued in corresponding International Patent Application No. PCT/US04/26505, dated Aug. 7, 2006.

Wu Y et al., "Artificial neural networks in mammography: application to decision making in the diagnosis of breast cancer," Radiology, 1st ed., Radiological Society of North America, vol. 187 ( No. 1), p. 81-87, ( Apr. 1993).

Giger et al., "Computerized detection of pulmonary nodules in computed tomography images," Investigative Radiology, J.P. Lippincott Company (Philadelphia), vol. 29 ( No. 4), p. 459-465, ( Apr. 1994).

Xu et al., "Development of an improved CAD sscheme for automated detection of lung nodulesin digital chest images," Medical Physics, American Association of Physical Medicine, vol. 24 ( No. 9), p. 1395-1404, ( Sep. 1997).

Chinese Office Action, with English translation, issued in Chinese Patent Application No. 2004800233519, mailed Dec. 25, 2009.

* cited by examiner

METHOD AND SYSTEM FOR INTELLIGENT QUALITATIVE AND QUANTITATIVE ANALYSIS FOR MEDICAL DIAGNOSIS

This Application is based on U.S. Provisional Application No. 60/494,802 filed Aug. 14, 2003, the entire content of which is hereby incorporated by reference.

BACKGROUND

1. Field of Invention

The present invention relates to systems and methods for medical information processing and analysis. Specifically, the present invention relates to intelligent qualitative and quantitative analysis of medical information for medical decision making.

2. Description of Related Art

In disease diagnosis using modern imaging techniques, physicians are often overwhelmed by the amount of information made available through different acquisition devices. Such devices may include, but are not limited to, ultrasound (US), Computerized Tomography (CT), and Magnet Resonance Imaging (MRI). Diagnostic information (DI), may differ from patient data and it may include key diagnostic evidence identified from diagnostic data that directly or indirectly supports and/or disaffirms a physician/specialist's hypothesis about a diagnosis. Often, important diagnostic information relevant to a specific disease is buried in the huge volume of data. In addition, although patient records and laboratory test results, such as blood tests, may provide important clues to suspected diseases/abnormalities, the interpretation of such information is not conventionally integrated with various image-based diagnosis processes in a coherent fashion. Consequently, physicians have to look manually for all disease-relevant information embedded in both non-visual and visual data from different sources. This task is labor intensive and requires a high level of skill. In addition, a manual process is also subject to mistakes, which may lead to misdiagnosis due to either negligence or lack of skill, qualitative and quantitative measurements, as well as intuitive visualization means that allow a physician to seamlessly integrate information across multi-modalities into a clinic workflow.

Another problem of the prior art is that conventional Computer Aided Detection/Diagnosis (CAD) systems usually allow a physician to access only either a computer's output in the form of binary decisions or raw data. That is, a wide variety of rich DI that can be derived between the raw data and the binary decision output (i.e., yes or no decisions) is ignored or discarded. Since such a loss is irreversible, the physician does not have the opportunity to interactively and quantitatively examine or identify suspicious regions, with the assistance of a computer system, in order to make their independent decision.

A third problem with conventional CAD systems is that multi-modality information, including both non-visual and visual information, is not utilized simultaneously. Current CAD systems usually operate on data of a single modality.

FIG. 1 illustrates a flowchart of a conventional computer-aided detection system, in which a physician starts, at 104, by selecting a patient image of a particular modality with respect to a pre-defined disease. At 106, a computer detects suspicious regions in the image that may correspond to where a specific disease manifests itself. The result of such computer detection is a binary yes/no decision for each location in the image. When the computer indicates the existence of an abnormality in an image location, a mark may be displayed, at 108, near the corresponding location in the image. At 110, the physician makes diagnostic decisions based on the computer derived marks.

BRIEF DESCRIPTION OF THE DRAWINGS

The present invention is further described in terms of exemplary embodiments, which will be described in detail with reference to the drawings. These drawings are non-limiting exemplary embodiments, in which like reference numerals represent similar parts throughout the several views of the drawings, and wherein.

DETAILED DESCRIPTION

An Intelligent Qualitative and Quantitative Analysis (IQQA) system is disclosed, which is aimed at systematically extracting and integrating diagnostic information from various sources. The system may be deployed on a general or a special purpose computer and adapted to any specific computing environment. The IQQA is a diagnostic-information-oriented computerized system that dynamically embeds different information processing and disease-specific applications into optimal clinical workflow. Such information processing and applications may include, but are not limited to, diagnostic data searching, diagnostic information (DI) extraction, DI quantification, DI visualization, DI fusion, as well as diagnosis of abnormalities and/or diseases based on data across multi-modality/multi-information type. Functionalities may be dynamically embedded through, for example, a) selectively activating functionalities based on a type of disease under investigation; b) dynamically forming a disease-specific workflow driven by specific diagnostic information available; and c) adaptively integrating physician's case-specific knowledge and experience of physicians gained during computer-human real-time interaction with previously built-in domain-specific knowledge to expand the knowledge base of the system in performing a diagnosis.

The IQQA system as described herein provides a wealth of information between raw diagnostic data and a binary diagnostic decision, thereby to assist physicians to make diagnostic decisions more effectively with potentially a higher precision. A Dynamic Matrix of Diagnostic Decision (dynamic MDD) platform, is designed to facilitate various functionalities such as extraction, presentation, navigation, visualization, fusion, and modification of, and interaction with diagnostic information.

Figure 1:
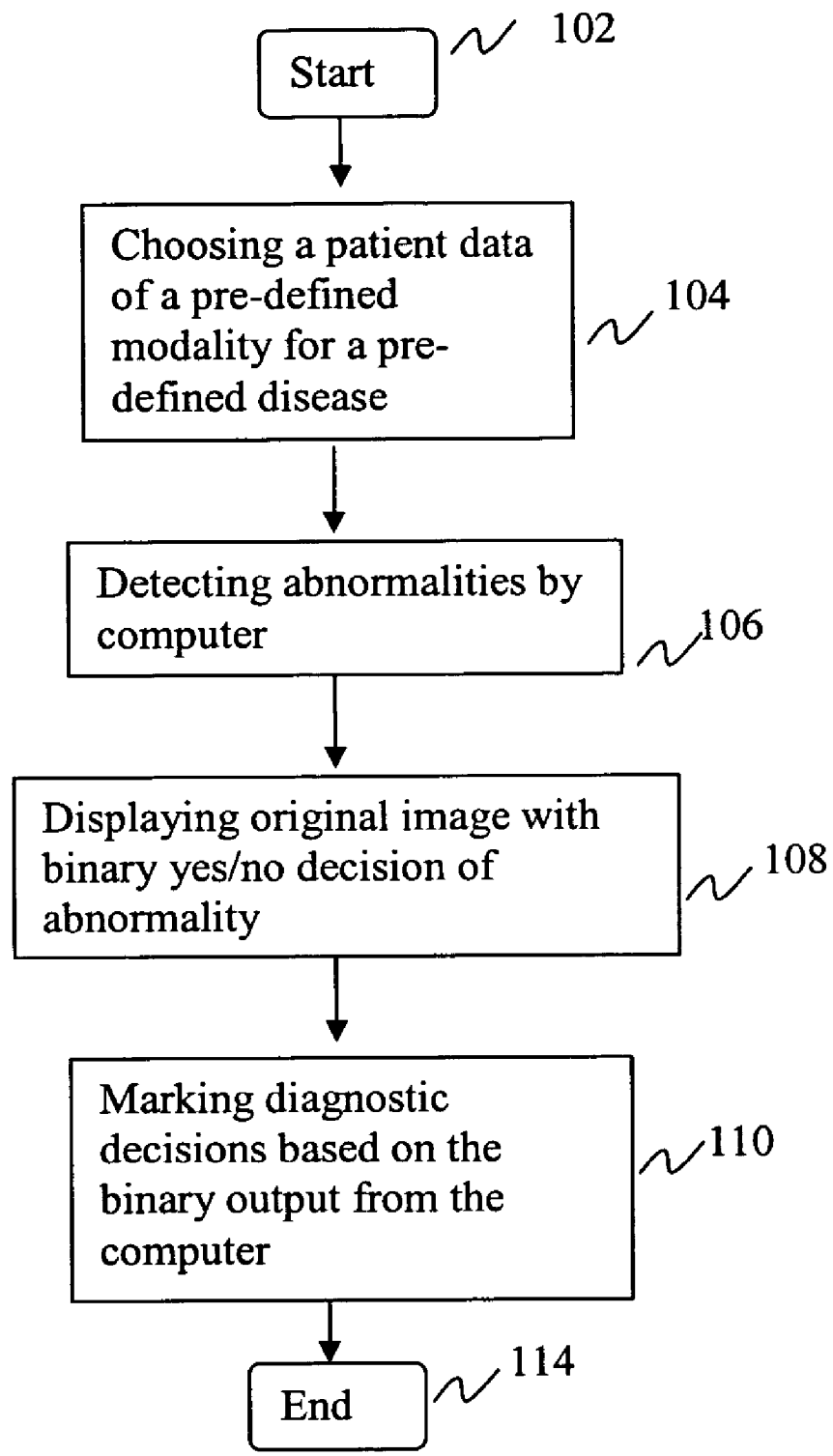
FIG. 1 illustrates a flowchart of a conventional computer-aided detection system.
Figure 2:
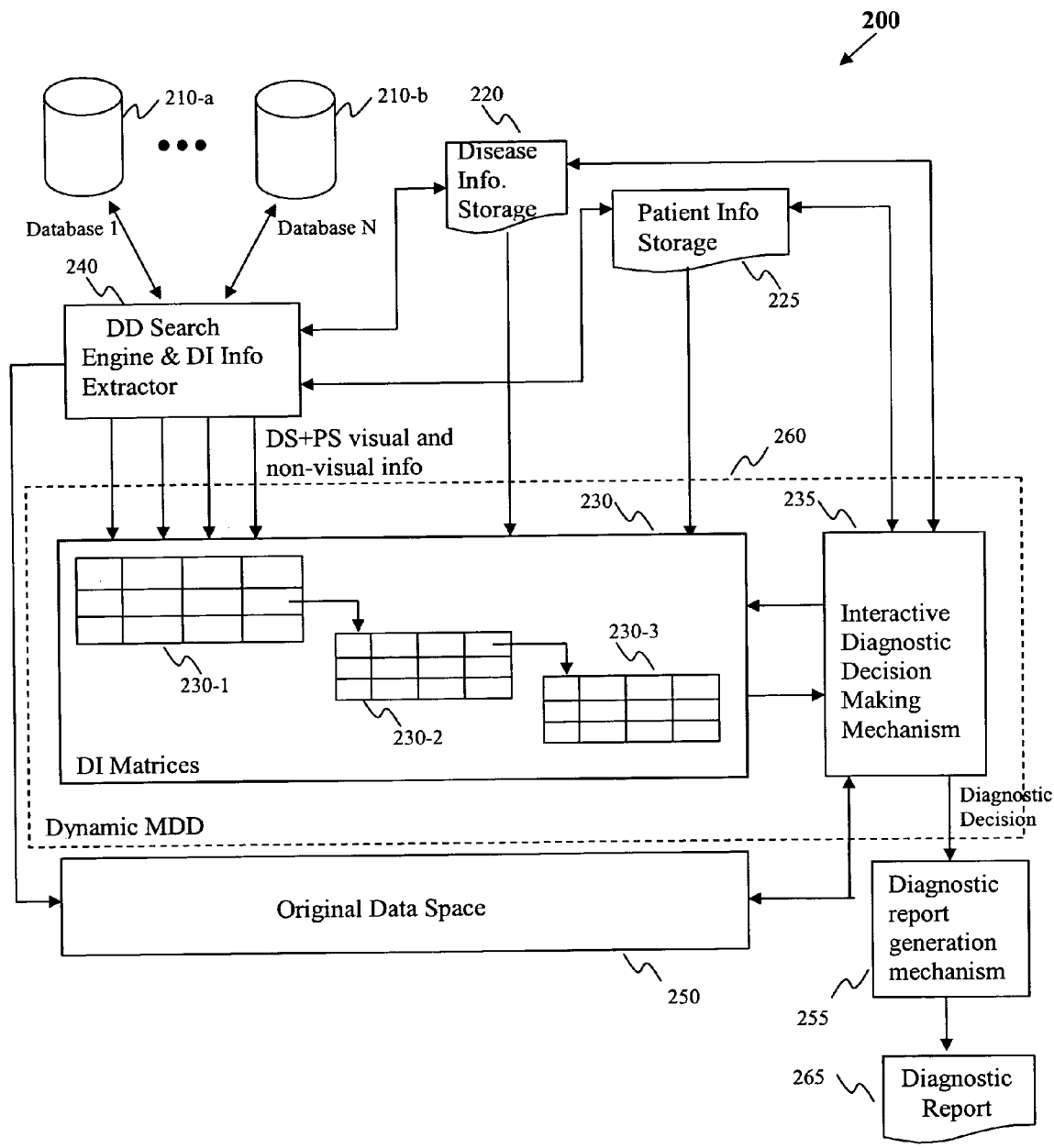
FIG. 2 depicts an exemplary high-level block diagram of an Intelligent Qualitative and Quantitative Analysis system, according to one embodiment of the present invention.

The IQQA as described herein provides an interactive, intelligent qualitative and quantitative analysis of diagnostic data across all modalities from different sources to assist physicians to make a diagnostic decision. FIG. 2 depicts an exemplary high level block diagram 200 of the IQQA, according to a preferred embodiment of the present invention. The system 200 comprises a patient info storage 225 and a disease info storage 225, a plurality of databases 210-a, ..., 210-b, a Diagnostic Data Search Engine and DI Extractor 240, a Dynamic Matrix of Diagnostic Decision (dynamic MDD) 260, an original data space 250, a diagnostic report generation mechanism 255, and a diagnostic report storage 265. The Dynamic MDD 260 comprises of a plurality of dynamic DI matrices 230-1, 230-2, and 230-1, and an Interactive Diagnostic Decision Making Mechanism (IDDM) 235.

In operation, a physician may first select a disease type, through the IDDM mechanism 235, from the disease information storage 220 and a patient ID or patient name from the patient information storage 225. Such information is used to start a patient-specific and disease-specific diagnostic data searching process. To do so, the patient information and disease information may be fed to the Diagnostic Data (DD) Search Engine and Diagnostic Information (DI) Extractor 240. The DD search engine and DI extractor 240 then searches for diagnostic data related to the given patient and disease from different databases, e.g., database 1 210-a, database N 210-b and extracts Disease Specific (DS) and Patient Specific (PS) DI, including visual and non-visual, from the searched diagnostic data. The databases searched may include local, remote, or distributed databases. Such databases may be accessible through any communication channels, including, but not limited to, a Local Area Network (LAN), a Wide Area Network (WAN), an Intranet, the Internet, a proprietary network, or a wireless network. The diagnosis decision produced by the IDDM mechanism 235 may be selectively fedback into the disease type storage 220 so that new disease types may be saved and utilized in the future.

Through the Dynamic Matrix of Diagnostic Decision (dynamic MDD) platform 260, the physician may make an interactive diagnostic decision. First, the extracted DI may be constructed in the form of DI matrices 230, which may be represented as a set of hierarchically organized dynamic matrices such as the dynamic DI matrix 1 230-1, the dynamic DI matrix 2 230-2, ..., and dynamic DI matrix i 230-3. The interactive diagnostic decision making mechanism 235 may facilitate the physician to explore the DI space, to perform DI extraction or re-extraction, DI modification, and/or DI fusion. The physician may rely on the dynamic diagnostic information represented by such matrices presented using interactive tools embedded in these dynamic MDDs 260 to reach a diagnostic decision. A diagnostic report 265 may also be generated through the diagnostic report generation mechanism 255.

Figure 3:
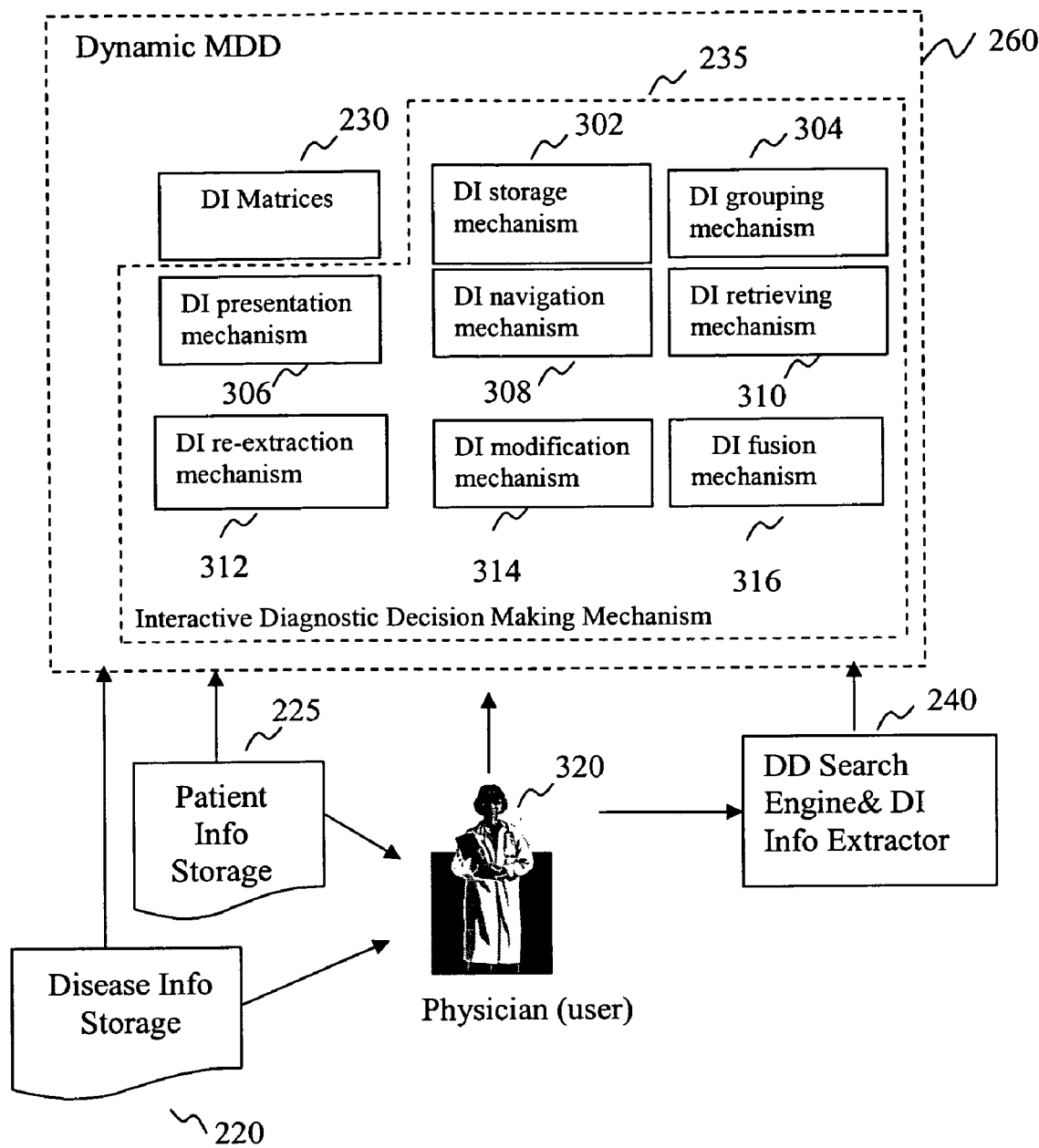
FIG. 3 depicts an exemplary construct of a Dynamic Matrix of Diagnostic Decision (Dynamic MDD) in relation to other parts of an Intelligent Qualitative and Quantitative Analysis system, according to one embodiment of the present invention.

FIG. 3 depicts an exemplary construct of the Dynamic Matrix of Diagnostic Decision (dynamic MDD) 260, according to an embodiment of the present invention. The Dynamic MDD 260 is a platform for physicians to perform real-time interactive diagnostic decision making. The Dynamic MDD 260 comprises a plurality of DI matrices 230, a DI storage mechanism 302, a DI grouping mechanism 304, a DI presentation mechanism 306, a DI navigation mechanism 308, a DI retrieving mechanism 310, a DI re-extraction mechanism 312, a DI modification mechanism 314, and a DI fusion mechanism 316.

The DI storage mechanism 302 is for storing diagnostic information. For example, for each suspicious region/volume of interest (ROI or VOI) associated with a specific disease, one or more dynamic DI matrices may be generated. These dynamic DI matrices may store key DI/evidence about the disease extracted from both non-visual and visual data around the ROI/VOI.

The DI grouping mechanism 304 is for organizing the extracted DI. Dynamic DI matrices 230 are a set of dynamically and hierarchically organized tables, constructed based on, e.g., anatomical, physiological, and biomedical knowledge and categories. It may also be grouped based on body parts, e.g., the entire body, a specific organ, some parts of the organ, biomarks, tissues, and molecules. Cells in the matrices may contain dynamic links to different sources of DI and/or the patient's raw diagnostic data. A matrix of a certain level may be embedded in its parent matrix at a higher level, except for the root matrix. Information contained in a matrix at each level may be systematically fused into its parent matrix one level above. The contained matrix hierarchy may be designed so that the most important diagnostic information related to making a diagnostic decision may be presented in the uppermost level, and more detailed DI information appears at lower levels. That is, an upper level matrix may provide an overview of the diagnostic information of the levels below, whereas the lower level matrices provide supporting information which further explains the items in the upper level table.

The DI presentation mechanism 306 is for presenting information in the DI matrices to the user in different forms. The DI in the Dynamic MDD may be presented either qualitatively or quantitatively. The presentation may be in a variety of formats, including, but are not limited to, numerals, strings, graphs, charts, colors, curves, and pictures. Representative images and results from computer analysis may be organized according to their relevance to the disease and may be directly visualized in one or more cells of a Dynamic DI matrix. The format and appearance of a Dynamic DI Matrix may be dynamically configured according to different criteria, such as the disease type selected, the image modality under examination, or the acquisition protocol. DI measurements that are considered abnormal may be highlighted using different colors in the dynamic DI matrices.

The DI navigation mechanism 308 provides means for a physician to explore the DI space. The DI may be organized in such a manner so that users may navigate in the DI space freely in real-time as needed. Through the DI navigation mechanism 308, a physician can explore information in DI matrices at any level by activating a desired matrix, bringing information into the physician's view via a simple mouse click on the corresponding items in the DI hierarchy. A user may also go back to the original DI data for re-examination or inspection, either qualitatively or quantitatively. In addition, a global view of the navigation trail may also be visualized while a user is exploring the DI space.

The DI retrieving mechanism 310 is for retrieving DI stored previously. The retrieved DI may be loaded into the Dynamic DI Matrices 230. A comparison between the current DI and previously stored DI may also be made.

The DI re-extraction mechanism 312 may be activated by a user to re-extract DI from previously saved ROI or VOI images to facilitate understanding and comparison with the current DI.

The DI modification mechanism 314 may be activated by a physician to make changes to extracted DI. For example, when a physician feels that a piece of DI extracted by the DD Search Engine and DI Extractor 240 is inaccurate or wrong, the physician may modify the DI by clicking on the corresponding cell in the dynamic DI matrix and then enter revisions. A set of interactive analytical tools and visualization tools encapsulated within the extracted visual DI may be activated and presented to the physician. The physician may then incorporate personal knowledge in the analysis procedure interactively. For example, a physician may interactively control the analysis/visualization tools through manual adjustment of their parameters. The physician may also directly edit certain items in the dynamic DI matrices and/or add new items and diagnostic comments into the matrices.

The DI fusion mechanism 316 for fusing domain-specific knowledge in the built-in IQQA system and a physician's case-specific knowledge. This may be achieved through a hierarchical decision making, man-machine real-time interaction and information exchanging process. In other words, dynamic MDD 260 in the IQQA makes all qualitative and quantitative diagnostic information transparent to physicians in their diagnostic decision making process. The information fusion methods provided by the DI fusion mechanism 316 are embedded in each hierarchical level of the DI presentation. Such fusion may also be performed across different levels. Disease-specific knowledge may be incorporated in the dynamic MDD 260 through information fusion, visualization and display. The DI fusion mechanism may employ patient and disease specific knowledge as well as non-patient specific disease specific knowledge to compute alert levels for each DI or abnormalities, lesions, cancers, or other diseases detected either by the system or by physicians. The dynamic MDD 260 may take into account a physician's preference and case-specific knowledge in a diagnostic decision making process by fusing the physician's knowledge with the built-in domain-specific knowledge in the IQQA system during the physician's real-time interaction with the dynamic MDD 260.

Figure 4:
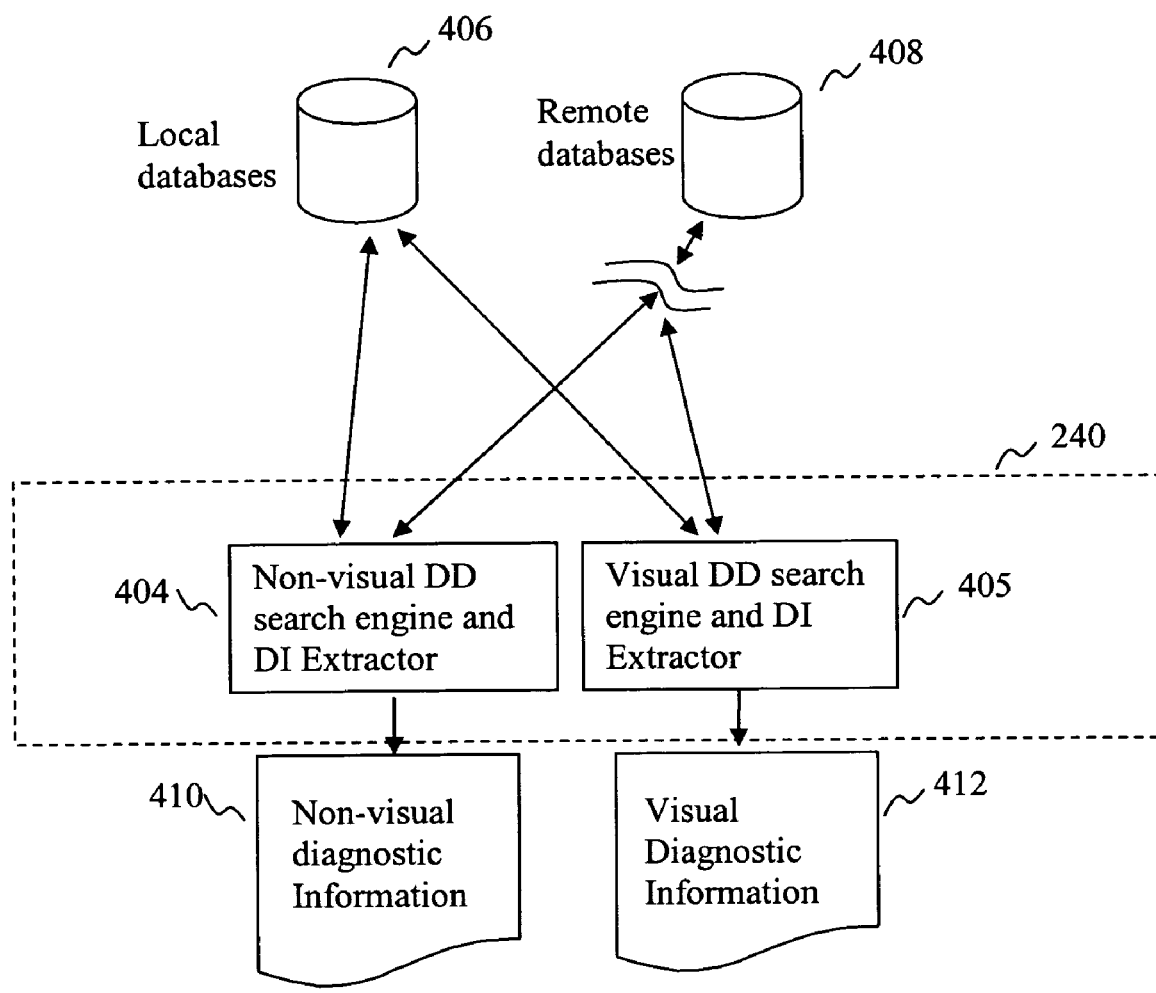
FIG. 4 shows an exemplary construct of a Diagnostic Data Search Engine and Diagnostic Info Extractor in relation to other parts, according to one embodiment of the present invention.

FIG. 4 shows an exemplary construct of the DD Search Engine and DI Info Extractor 240 in relation to other parts, according to one embodiment of the present invention. A non-visual DD Search Engine and DI Exactor 404 may search different databases 406-408 for non-visual diagnostic data and extract non-visual diagnostic information 410. Such databases may include local, remote, and distributed databases, and may be accessed through a communication channel. A visual DD Search Engine and DI Extractor 405 may search the databases 406-408 for visual diagnostic data and extract visual diagnostic information 412.

In addition to patient specific data, the non-visual DD Search Engine and DI extractor 404 may also search for non-patient-specific, but disease specific information across the different databases to, for example, bring the most up-to-date statistics about the disease into the IQQA decision support process. Such information may be utilized in different ways. For example, such information may be integrated in the IQQA's qualitative and quantitative analysis process. Knowledge about the disease may also be used to build and update any internal diagnostic model for a corresponding disease within IQQA. Furthermore, when physicians have direct access to such up-to-date statistical information about specific diseases, they can interpret the information, based on his/her own experience and knowledge, and rely on such interpretation in the decision making process.

The search results returned by the DD Search Engine and DI extractor 240 may be presented to a user in the form of, for example, file trees. The user may choose one of the files for further review. Alternatively, the user may exercise discretion to view all the studies in a sequential fashion. Those disease and patient specific, disease and non-patient specific diagnostic data may include both non-visual data or visual data. Non-visual data may comprise patient record, blood test results, and genotype data. Visual data may comprise diagnostic images of different modalities (e.g., CT, MRI, X-ray), and pathological images.

Figure 5:
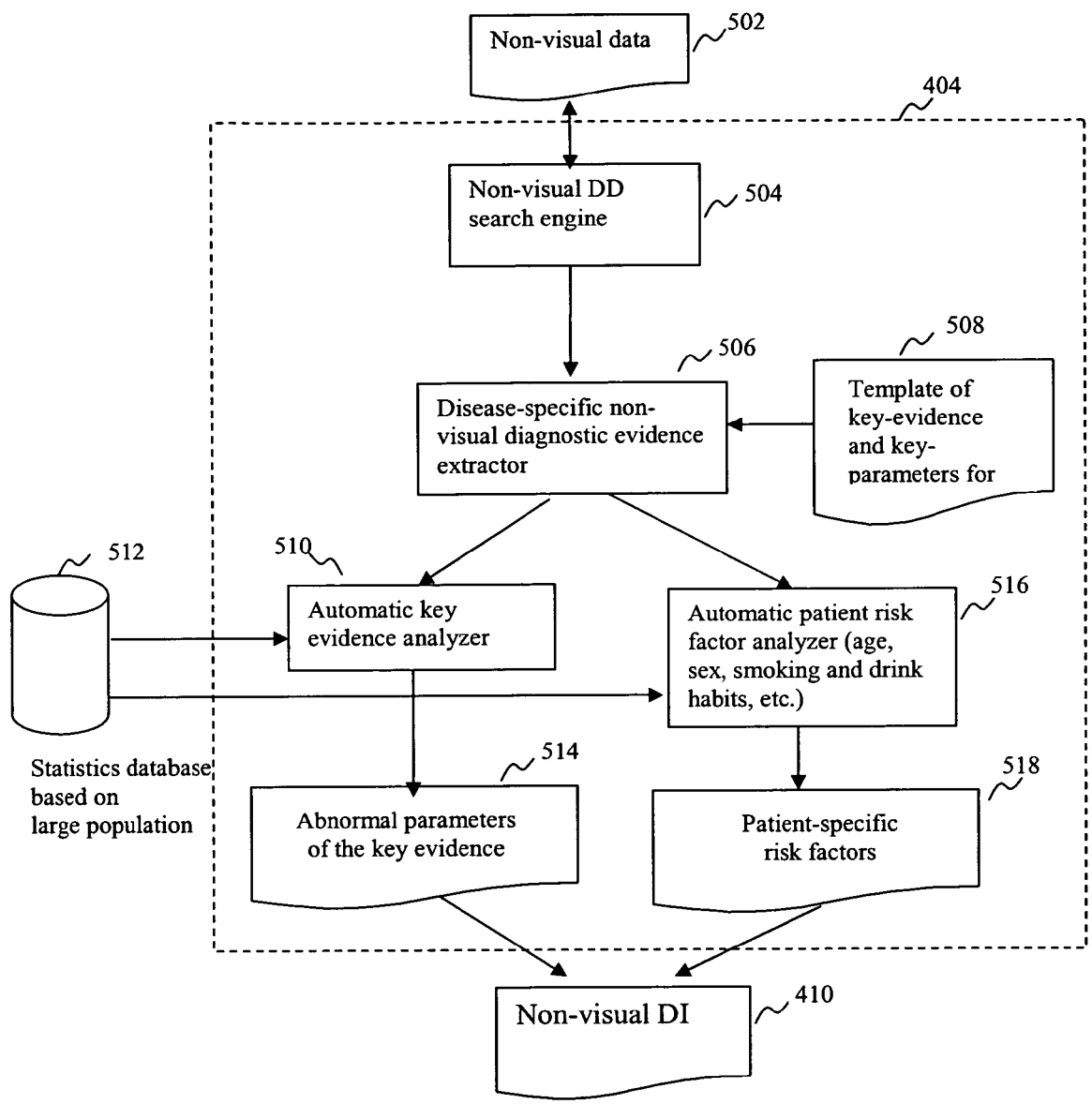
FIG. 5 shows an exemplary construct of a non-visual Diagnostic Data Search Engine and DI Extractor in relation to other parts, according to one embodiment of the present invention.

FIG. 5 shows an exemplary construct of the non-visual DD search engine and DI extractor 404 in relation to other parts, according to one embodiment of the invention. A non-visual data search engine 504 is deployed to search for non-visual diagnostic data. Such a search engine may be any commercial or off-the-shelf search engine, implemented in any language such as SQL. Based on the searched non-visual data, a disease-specific non-visual diagnostic evidence extractor 506 may extract one or more pieces of disease-specific key evidence. Such extraction may be guided by a disease-specific evidence template 508 that pre-defines what constitutes key evidence given a disease type. After the key evidence is extracted, an automatic key evidence analyzer 510 may be used to analyze the key evidence. Statistical measurements of corresponding evidence may be retrieved from a database 512 and used to evaluate the extracted key evidence. Such statistical measurements may be derived based on studies over a statistically significant population so that they can be used to evaluate the significance of the key evidence extracted. For example, each piece of patient specific key evidence may be compared with the statistical range of the same evidence present in the database 512. Evidences with measures that are beyond the given normal range, 514, may then be stored in a non-visual DI storage 410.

In addition to the key evidence analysis, a risk factor analyzer 516 may further analyze the risk factors associated with the patient with respect to the given a disease type based on information related to the patient, such as age, sex, medication record, blood test or family history. The output 518 of such analysis may also provide estimated degrees of impact of these risk factors on the hypothesized disease or lesion.

Figure 6:
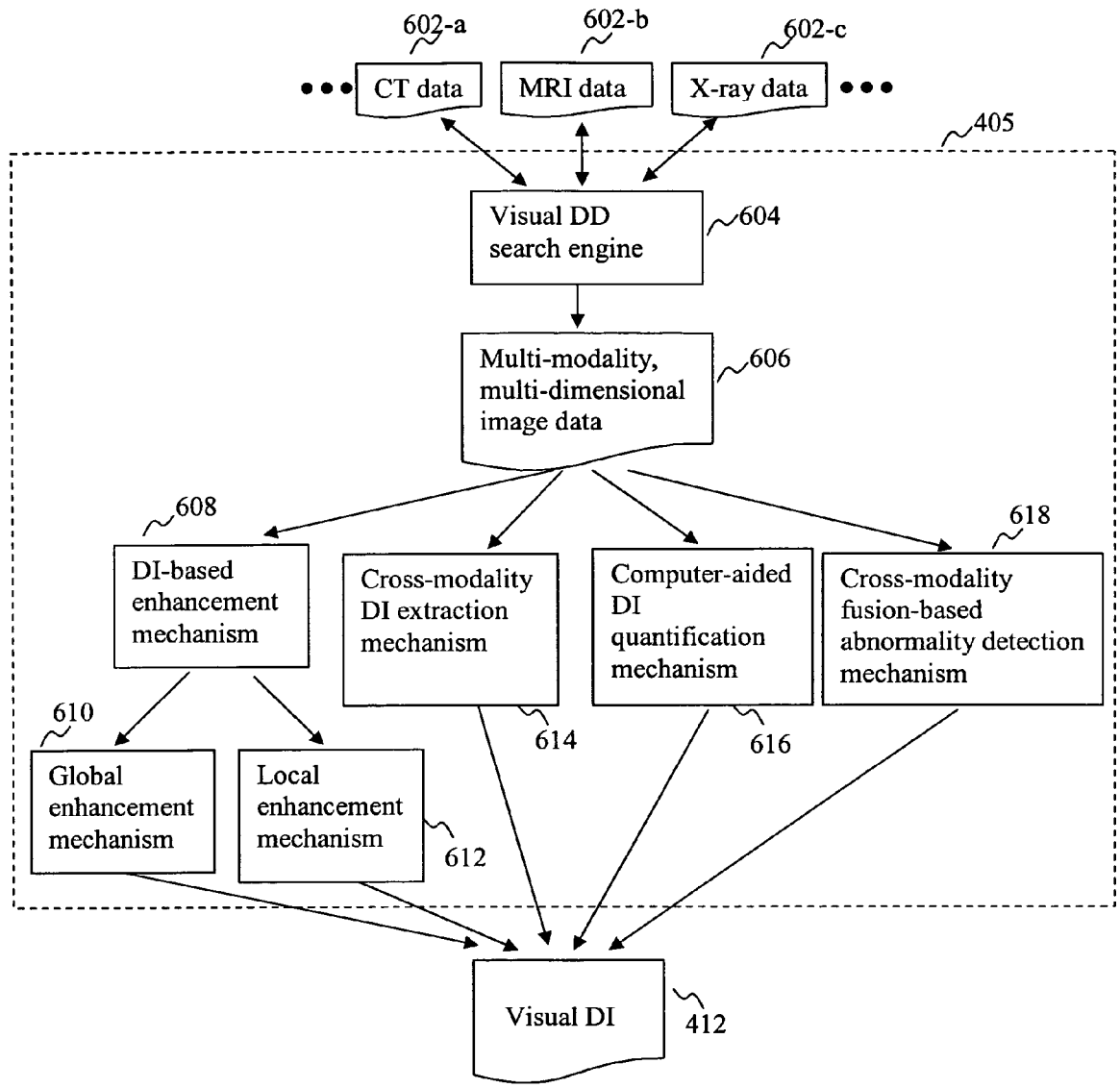
FIG. 6 shows an exemplary construct of a visual Diagnostic Data Search Engine and DI Extractor in relation to other parts, according to one embodiment of the present invention.

FIG. 6 shows an exemplary construct of the visual DD search engine and DI extractor 405 according to an embodiment of the present invention. A visual DD search engine 604 performs a search for all visual data related to specific patient and disease, such as, CT data, MRI data, and X-ray data. Such data forms a multi-modality, multi-dimensional data set 606. Here multi-dimensionality may include both spatial and temporal dimensions. Various visual DI extraction functions, according to the present invention, may be performed while a physician navigates through an imagery subspace, e.g., in selected 2D, 3D, 4D, or higher dimensional sub-space created by each of the modalities in real-time or near real-time interactively.

In the depicted exemplary embodiment, there comprises a DI-based enhancement mechanism 608, a cross-modality DI extraction mechanism 614, a computer-aided DI quantification mechanism 616, and a cross-modality fusion-based abnormality detection mechanism 618. These visual DI extractors may extract both qualitative and quantitative diagnostic information. For example, to obtain qualitative visual DI, the DI-based enhancement mechanism 608 enhances diagnostic information contained in the imageries. Based on global or local anatomic and disease information as well as information extracted in corresponding locations of other imageries, the DI-based enhancement mechanism 608 may automatically determine what is the most focused DI for the given specific disease in the given image and compute feature statistics about suspicious regions detected either by the system or by the user. Such statistics may be used to automatically set the enhancement parameters to bring the best visible diagnostic information to the eyes of a physician for diagnosis purposes. A user can choose to apply a global disease-specific enhancement via a global enhancement mechanism 610 to enhance an entire image set, based on information gathered from both non-visual DI and other available visual DI, including, but not limited to, statistics about shape, size, and brightness of all suspicious regions. A user can also choose to use a local enhancement mechanism 612 to enhance each local suspicious region of interest. Parameters used in enhancement may be computed based on DI information about individual suspicious region of interest and the disease.

Visual DI may also be extracted via the cross-modality DI extraction process 614. Multi-modality and multi-dimensional information may be exploited in such a way that DI extracted from one modality or dimension may be used to confirm or disaffirm DI in another modality or dimension. Patient and disease specific, as well as non-patient specific and disease specific non-visual information may also be used to aid such visual DI extraction process. For example, age and sex may be used to determine focus regions of suspicion for a specific disease. Visual DI extraction and/or re-extraction may be performed automatically or interactively in real-time by physicians. In an interactive extraction process, a physician may apply his/her own knowledge to the extraction process. For example, a physician may make some manual adjustment to already extracted DI by adjusting parameters that are used by the DI extraction process.

Visual DI may also be quantified via the computer-aided DI quantification (CAQ) mechanism 616. The CAQ mechanism 616 is capable of automatically quantifying DI across multiple modalities. Such quantification may be applied to measurements such as size, shape, and intensity variations of suspicious regions within and across multimodalities.

Visual DI may also be extracted via the cross-modality fusion-based abnormality detection mechanism 618. A physician may pose different hypotheses or sub-hypotheses about diseases, including both disease type and disease location, to the system based upon, e.g., spatial reasoning or temporal reasoning about the extracted DI in the hierarchically organized DI space. Cross-modality fusion, according to the present invention, may be performed in different modes. For example, fusion can be performed based on positional or DI information. In the positional fusion mode, visual data cross different modalities and dimensions are registered prior to the fusion. In a DI fusion mode, fusion is based on the nature of the information contained in the DI space.

Figure 7:
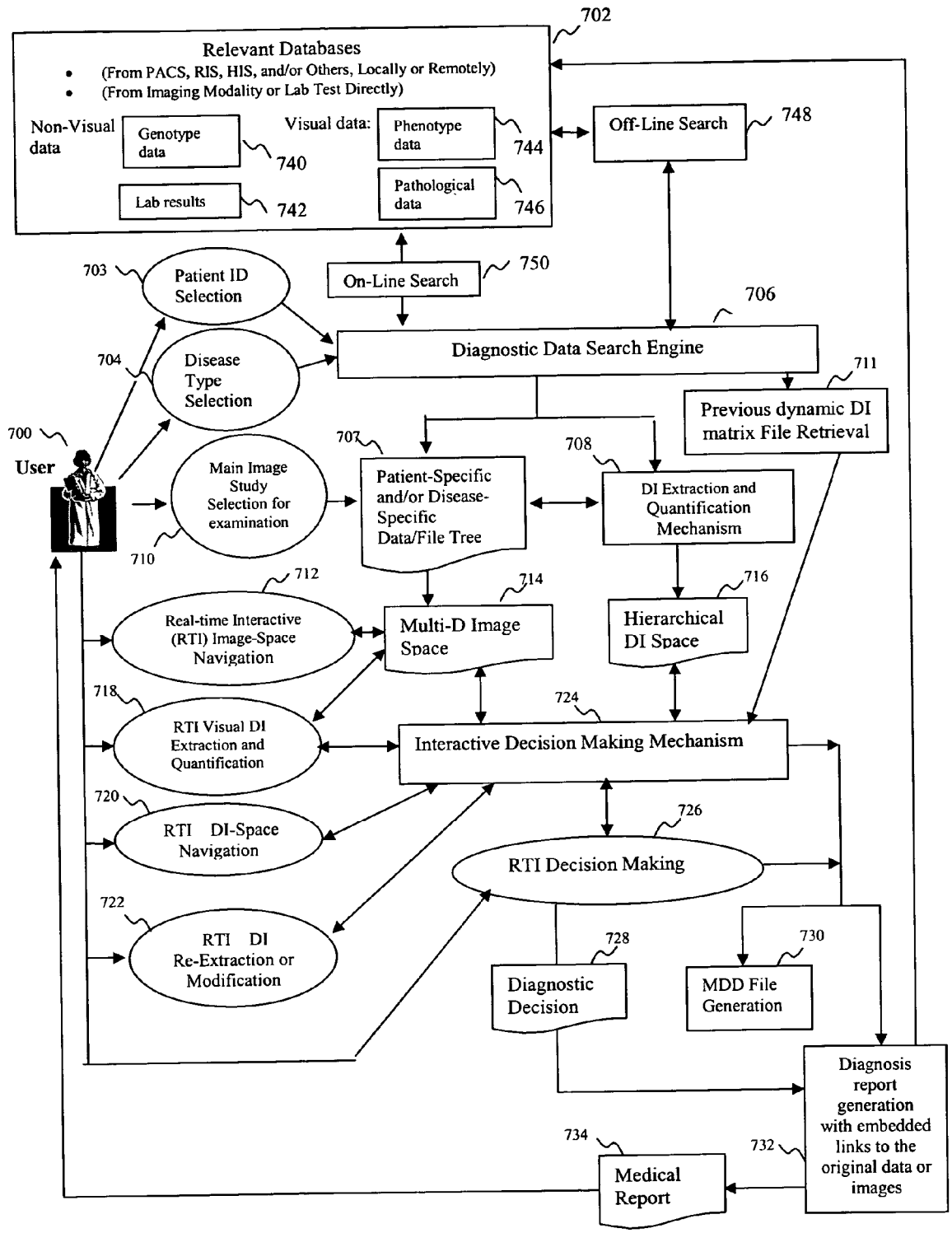
FIG. 7 illustrates the overall operation of an IQQA system, according one embodiment of the invention.

FIG. 7 illustrates the overall operational scheme of the IQQA system, according one embodiment of the invention. First, a user 700 selects a patient ID from an existing patient ID list, or enter a patient ID 703. The user may also select a disease type 704. With the patient ID 703 and disease type 704, a Diagnostic Data Search Engine 706 automatically identifies all available diagnostic data, both patient-specific and non-patient specific, that is relevant to the specified disease from one or more relevant databases 702, either local, remote, or distributed. Such identified diagnostic data may be non-visual or visual, including genotype data 740, lab test results 742, phenotype data 744, and pathological data 746. The retrieved patient and non-patient specific and disease-specific data may then be organized according to some pre-defined criteria. For example, data type and date of examination may be used to organize the retrieved data.

The search for diagnostic data may be conducted via an on-line search 750 or via an off-line search 748. An on-line search may be performed while a physician interacts with the IQQA system during a diagnostic decision making process. An off-line search may be performed before the physician starts the diagnosis process via the IQQA system. The search results may be presented to the user in the form of, for example, file trees 707 so that a user may choose one or more of the files for further review (710). A DI extraction and quantification mechanism 708 may extract diagnostic information from the diagnostic data with respect to the specified disease. The patient and disease-specific, as well as non-patient specific and disease specific data and the extracted diagnostic information may be made accessible to a user during a diagnosis session. The user may manually examine, if needed simultaneously, all the accessible diagnostic data and diagnostic information associated with the selected patient at the same time.

The extracted diagnostic information may then be organized hierarchically in one or more dynamic DI matrix/matrices in a diagnostic information space 716 according to some pre-determined criteria such as degree of details of the lesion, parts of the body where disease occurs.

The user 700 may further interact with the dynamic DI matrices in the diagnostic information space 716 via an interactive decision making mechanism 724. The user 700 may also choose to load dynamic DI matrices generated from previous exams 711 of the same patient and merged with the current DI matrices. Decisions may be made also in the context of the previous DI matrices.

The dynamic DI matrices in the DI space 716 offers an information space where a physician may navigate to identify rich information from different modalities and along different dimensions, all at different levels of detail. A physician may navigate in the diagnostic information space 716 in a Real-Time Interactive (RTI) mode in either an imagery sub-space or a DI sub-space. The imagery sub-space may further include 2D image sub-space, 3D image sub-space, or image sub-space in higher dimensions. A physician may select to operate in any sub-space according to needs. While navigating in the diagnostic information space 716, a user may also navigate at different levels of detail, exploring and searching for diagnostic information that may be relevant to diagnostic decision making.

Diagnostic information may be presented to the user 700 after appropriate processing such as information fusion, visualization, and real-time user interaction of the dynamic MDD. The user 700 may perform RTI image space navigation 712, RTI visual DI extraction and quantification 718, or RTI DI-space navigation 720. During real time user interaction, the user 700 may also re-extract existing DI or make modifications to existing DI (722). Through RTI decision making 726, the user can make diagnostic decisions 728.

Information contained in different dynamic DI matrices may be compiled to generate a report 734 by a diagnostic report generation mechanism 732. Such a generated report may be particularly structured based on some specified requirements, which may be automatically set up as default or may be dynamically updated by the user 700. The generated report 734 may contain hyperlinks associated with a medical decision included in the report 734 connecting to the original images or other diagnostic information that are used in reaching the underlying medical decision. The hyperlinks included in the report 734 may also embed some integrated mechanisms that may be launched to provide the capability of displaying, navigation, or reviewing of the supporting diagnostic information. When the user 700 completes the examination, the dynamic DI matrices 730 derived during the current examination may be stored for future use.

Figure 8:
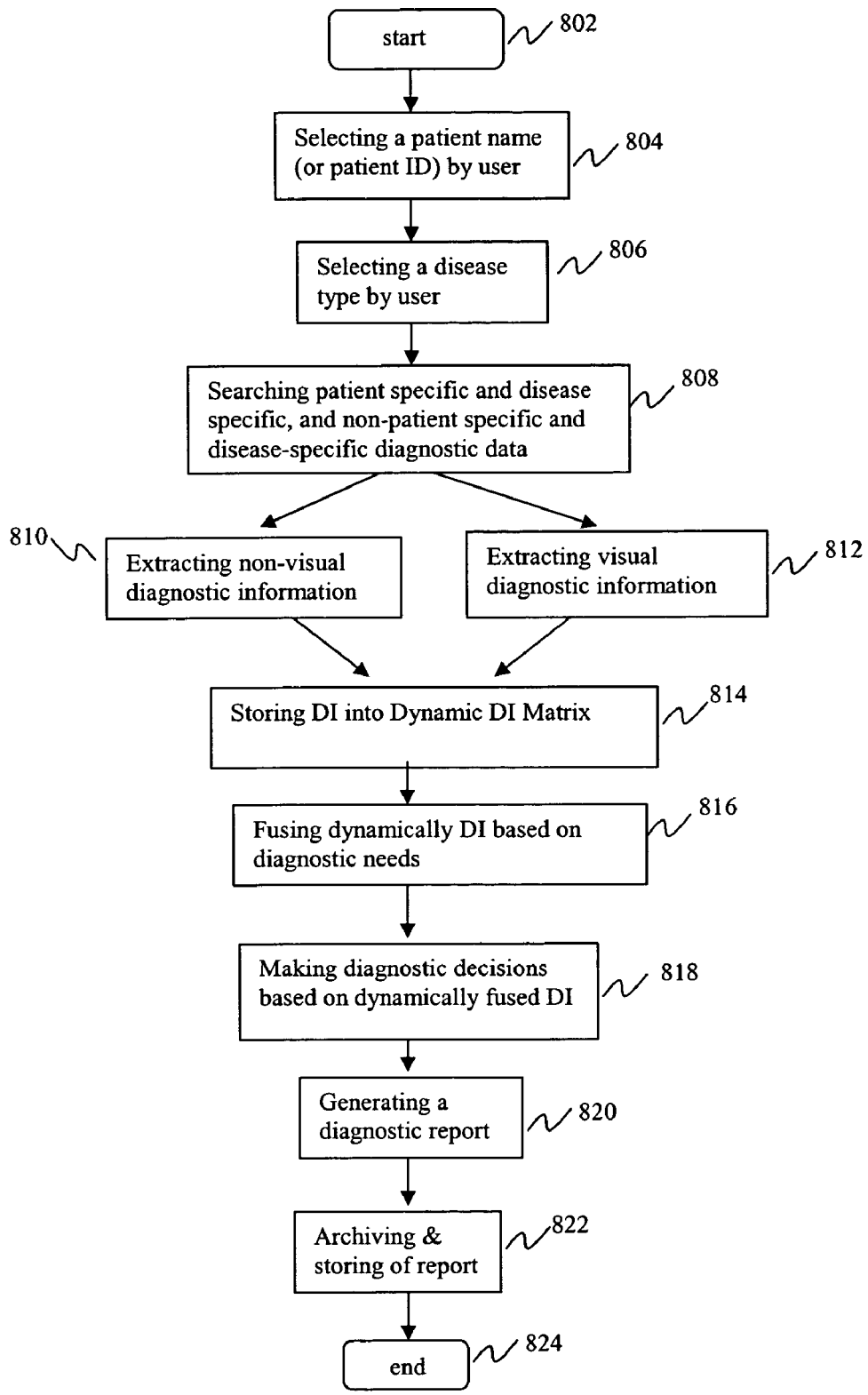
FIG. 8 is a flowchart of an exemplary process, in which an intelligent qualitative and quantitative analysis system facilitates a user to perform patient-specific and disease-specific multimodality diagnostic information based medical decision making, according to one embodiment of the present invention.

FIG. 8 is a flowchart of an exemplary process, in which the IQQA system facilitates a user to reach a medical decision using diagnostic information from different sources, according to one embodiment of the invention. After the system is started, a user may select a patient name or patient ID at 804, and a disease type at 806. At 808, patient-specific and disease-specific, and non-patient-specific and disease-specific diagnostic data is retrieved from one or more databases. From the diagnostic data, non-visual DI may be extracted at 810, and visual DI may be extracted at 812. The extracted DI is stored in dynamic DI matrices at 814. Based on the extracted DI from different sources, modalities, and dimensions, dynamic fusion is performed based on diagnostic needs at 816. Such a dynamic fusion may be carried out via either an automatic or an interactive process. At 818, diagnostic decisions may then be made based on the dynamically fused DI. At 820, a diagnostic report is generated. Such a report may include information automatically generated based on DI, such as summary of key evidence or statistics. The generated report may also include information entered by a physician. After a physician makes relevant diagnostic decisions, associated DI may be archived and stored, at 822, for future reference.

What is claimed is:

1. A method implemented on at least one machine each of which has at least one processor, storage, and communication platform for computer aided medical diagnosis, comprising:
   obtaining, from a user via a user interface, identifying information to be used to obtain medically-related information;
   obtaining, automatically via a search engine, the medically-related information from different sources based on the identifying information;
   automatically forming, via a dynamic diagnostic decision matrix platform, a plurality of hierarchically arranged matrices of diagnostic information in a hierarchy, where a matrix at each level in the hierarchy is an assembly of organized medically-related information and generated by dynamically fusing different types of medically-related information from lower levels of the hierarchy, and each node in the hierarchy embeds a tool that can be activated when the diagnostic information is displayed;
   modifying, via the dynamic diagnostic decision matrix platform, diagnostic information stored in at least one of the plurality of hierarchically arranged matrices;
   updating, via the dynamic diagnostic decision matrix platform, the at least one hierarchically arranged matrix based on the modified diagnostic information stored therein to form updated hierarchically arranged matrices; and
   computing, via the machine processor, a medical decision based on the updated hierarchically arranged matrices of diagnostic information, wherein
      diagnostic information at any node of any level in the hierarchy is accessible and can be manipulated by the user interactively based on a data manipulation tool embedded with the diagnostic information,
      diagnostic information at a level of the hierarchy can be dynamically fused with that at a same or a different level of the hierarchy based on a tool embedded with the diagnostic information, and
      a result of the fusing is propagated within the hierarchy.

2. The method according to claim 1, wherein the identifying information includes a patient identification and a disease type.

3. The method according to claim 2, wherein the different types of the medically-related information and the result derived from an analysis of any of the different types of the medically-related information used in said fusing are determined dynamically based on the disease type.

4. The method according to claim 2, wherein the different types of the medically-related information and the result derived from an analysis of any of the different types of the medically-related information used in said fusing are determined dynamically based on both the disease type and the patient identification.

5. The method according to claim 2, wherein the different types of the medically-related information and the result derived from an analysis of any of the different types of the medically-related information used in said fusing are determined in one of an automatic mode and an interactive mode.

6. The method according to claim 2, further comprising analyzing the medically-related information to produce the result derived from an analysis of any of the different types of the medically-related information associated with the disease type.

7. The method according to claim 6, wherein said analyzing comprises at least one of:
   enhancing the medically-related information;
   extracting diagnostic evidence associated with the disease type from the medically-related information and/or the enhanced information thereof;
   evaluating a feature derived from the medically-related information;
   detecting an abnormality candidate based on the medically-related information; and
   identifying patient-specific risk factors based on the medically-related information.

8. The method according to claim 7, wherein said enhancing includes at least one of:
   enhancing a part of a medical image contained in the medically-related information; and
   enhancing an entire medical image contained in the medically-related information.

9. The method according to claim 7, wherein said extracting is performed across different modalities of the medically-related information.

10. The method according to claim 7, wherein the diagnostic evidence to be extracted is determined in one of an automated mode and an interactive mode.

11. The method according to claim 7, wherein said evaluating is performed in one of an automated mode and an interactive mode.

12. The method according to claim 11, wherein said evaluating is one of qualitative evaluating and a quantitative evaluating.

13. The method according to claim 12, wherein the quantitative evaluating includes at least one of:
   estimating size of a region in a medical image corresponding to an abnormality;
   estimating statistics related to intensity distribution within a region of the abnormality;
   determining a change with respect to an aspect of the abnormality occurred over time;
   determining shape of the abnormality; and
   determining texture of the abnormality.

14. The method according to claim 1, wherein the medically-related information includes patient-specific and disease-specific information.

15. The method according to claim 1, wherein the medically-related information includes non-patient-specific and disease-specific information.

16. The method according to claim 1, wherein the medically-related information includes visual medical information and non-visual information.

17. The method according to claim 16, wherein the non-visual information includes at least one of:
   a medical test result;
   genotype information; personal medical history;
   risk factors related to personal life style and behaviors;
   phenotype or pathological information; family medical history; and
   general medical knowledge.

18. The method according to claim 16, wherein the visual medical information includes medical images acquired in a space of a certain dimension.

19. The method according to claim 18, wherein the certain dimension of the space includes at least one of two-dimensions and three-dimensions.

20. The method according to claim 1, wherein the different sources include:
   a CT scan;
   an X-ray examination;
   a PET scan;
   a SPECT scan;
   a nuclear medicine examination;
   an MRI scan;
   a sonogram;
   a DNA or molecular imaging procedure;
   a blood test;
   a physical examination; and
   any combination thereof.

21. The method according to claim 1, wherein a matrix at a lower level of the hierarchy represents more detailed diagnostic information.

22. The method according to claim 1, wherein said fusing combines different types of the medically-related information in different modalities.

23. The method according to claim 1, wherein the medical decision is a diagnostic decision.

24. The method according to claim 1, further comprising navigating through information contained in the at least one matrix of diagnostic information.

25. The method according to claim 1, further comprising generating a report based on the medical decision.

26. The method according to claim 25, wherein the report reporting the medical decision includes a link connecting the medical decision to diagnostic information represented in the at least one matrix and based on which the medical decision is made.

27. A system for computer aided medical diagnosis, comprising:
   an interface configured to facilitate to obtain identifying information to be used to obtain medically-related information;
   a search engine configured to obtain, automatically, the medically-related information from different sources based on the identifying information; and
   a dynamic diagnostic decision matrix platform configured to:
      automatically form a plurality of hierarchically arranged matrices of diagnostic information in a hierarchy, where a matrix at each level in the hierarchy is an assembly of organized medically-related information and generated by dynamically fusing different types of medically-related information from lower levels of the hierarchy, and each node in the hierarchy embeds a tool that can be activated when the diagnostic information is displayed,
      modify diagnostic information stored in at least one of the plurality of hierarchically arranged matrices,
      update the at least one hierarchically arranged matrix based on the modified diagnostic information stored therein to form updated hierarchically arranged matrices, and
      compute, via a machine processor, a medical decision based on the updated hierarchically arranged matrices of diagnostic information, wherein
         diagnostic information at any node of any level in the hierarchy is accessible and can be manipulated by a user interactively based on a data manipulation tool embedded with the diagnostic information,
         diagnostic information at a level of the hierarchy can be dynamically fused with that at a same or a different level of the hierarchy based on a tool embedded with the diagnostic information, and
         a result of the fusing is propagated within the hierarchy.

28. The system according to claim 27, wherein the identifying information includes patient identification information and disease information.

29. The system according to claim 28, wherein the search engine searches patient-specific and disease-specific medically-related information with respect to a selected patient identification and a selected disease type.

30. The system according to claim 27, wherein the search engine searches non-patient -specific and disease-specific medically-related information associated with a selected disease type.

31. The system according to claim 27, further comprising a diagnostic information extractor configured to analyze the medically-related information and identify, from the medically-related information, medical evidence associated with a selected disease type.

32. The system according to claim 31, wherein the diagnostic information extractor comprises a non-visual diagnostic information extractor and a visual diagnostic information extractor.

33. The system according to claim 32, wherein the non-visual diagnostic information extractor includes at least one of:
   a disease-specific non-visual diagnostic evidence extractor configured to extract diagnostic evidence associated with a disease type from the medically-related information; and
   a patient-specific risk factor analyzer configured to identify patient-specific risk factors based on the medically-related information.

34. The system according to claim 32, wherein the visual diagnostic information extractor includes at least one of:
   an enhancement mechanism configured to enhance the medically-related information;
   a visual diagnostic evidence extractor configured to extract diagnostic evidence associated with the disease type from visual information contained in the medically-related information and/or the enhanced information thereof;
   an evaluation mechanism configured to evaluate diagnostic evidence derived from the medically-related information; and
   an abnormality detection mechanism configured to detect an abnormality candidate based on the medically-related information.

35. The system according to claim 34, wherein the enhancement mechanism includes:
- a local enhancement mechanism capable of enhancing a part of a medical image contained in the medically-related information; and
- a global enhancement mechanism capable of enhancing an entire medical image contained in the medically-related information.

36. The system according to claim 27, wherein the dynamic diagnostic decision matrix platform comprises:
- a diagnostic information storage unit configured to store diagnostic information extracted from the medically-related information;
- a diagnostic information management mechanism configured to manage access to the diagnostic information storage;
- a diagnostic information navigation mechanism configured to facilitate navigating through diagnostic information represented by the at least one matrix; and
- a diagnostic evidence identification mechanism configured to identify diagnostic evidence from the at least one matrix of diagnostic information.

37. The system according to claim 36, wherein the diagnostic evidence identification mechanism includes
- a diagnostic information fusion mechanism configured to fuse different types of the medically-related information in at least one modality;
- a diagnostic information modification mechanism configured to modify diagnostic information; and
- a diagnostic evidence extraction mechanism configured to extract diagnostic evidence from at least one of the medically-related information, the fused information, and the modified information.

38. The system according to claim 36, wherein the diagnostic evidence identification mechanism is implemented in one of an automated mode and an interactive mode.

39. The system according to claim 27, further comprising a medical report generation mechanism configured to produce a medical report reporting the medical decision.

40. The system according to claim 39, wherein the medical report includes links connecting to diagnostic information contained in the at least one matrix of diagnostic information that is used to reach the medical decision.

41. A machine readable medium having instructions stored thereon where the instructions, when accessed, enable the following:
- obtaining, from a user via a user interface, identifying information to be used to obtain medically-related information;
- obtaining, automatically via a search engine, the medically-related information from different sources based on the identifying information;
- automatically forming, via a dynamic diagnostic decision matrix platform, a plurality of hierarchically arranged matrices of diagnostic information in a hierarchy, where a matrix at each level in the hierarchy is an assembly of organized medically-related information and generated by dynamically fusing different types of medically-related information from lower levels of the hierarchy, and each node in the hierarchy embeds a tool that can be activated when the diagnostic information is displayed;
- modifying, via the dynamic diagnostic decision matrix platform, diagnostic information stored in at least one of the plurality of hierarchically arranged matrices:
- updating, via the dynamic diagnostic decision matrix platform, the at least one hierarchically arranged matrix based on the modified diagnostic information stored therein to form updated hierarchically arranged matrices; and
- computing, via a machine processor, a medical decision based on the updated hierarchically arranged matrices of diagnostic information, wherein,
  - diagnostic information at any node of any level in the hierarchy is accessible and can be manipulated by the user interactively based on a data manipulation tool embedded with the diagnostic information,
  - diagnostic information at a level of the hierarchy can be dynamically fused with that at a same or a different level of the hierarchy based on a tool embedded with the diagnostic information, and
  - a result of the fusing is propagated within the hierarchy.

42. The medium according to claim 41, wherein the identifying information includes a patient identification and a disease type.

43. The medium according to claim 42, wherein the different types of the medically-related information and the result derived from an analysis of any of the different types of the medically-related information used in said fusing are determined dynamically based on the disease type.

44. The medium according to claim 42, wherein the different types of the medically-related information and the result derived from an analysis of any of the different types of the medically-related information used in said fusing are determined dynamically based on both the disease type and the patient identification.

45. The medium according to claim 42, wherein the different types of the medically-related information and the result derived from an analysis of any of the different types of the medically-related information used in said fusing are determined in one of an automatic mode and an interactive mode.

46. The medium according to claim 42, the instructions, when accessed, further enable analyzing the medically-related information to produce the result derived from an analysis of any of the different types of the medically-related information associated with the disease type.

47. The medium according to claim 46, wherein said analyzing comprises at least one of:
- enhancing the medically-related information;
- extracting diagnostic evidence associated with the disease type from the medically-related information and/or the enhanced information thereof;
- evaluating a feature derived from the medically-related information;
- detecting an abnormality candidate based on the medically-related information; and
- identifying patient-specific risk factors based on the medically-related information.

48. The medium according to claim 47, wherein the diagnostic evidence to be extracted is determined in one of an automated mode and an interactive mode.

49. The medium according to claim 47, wherein said evaluating is performed in one of an automated mode and an interactive mode.

50. The medium according to claim 47, wherein said evaluating is one of qualitative evaluating and a quantitative evaluating.

51. The medium according to claim 50, wherein the quantitative evaluating includes at least one of:
- estimating size of a region in a medical image corresponding to an abnormality;
- estimating statistics related to intensity distribution within a region of the abnormality;

determining a change with respect to an aspect of the abnormality occurred over time;
determining shape of the abnormality; and
determining texture of the abnormality.

52. The medium according to claim 41, wherein the medically-related information includes visual medical information and non-visual information.

53. The medium according to claim 52, wherein the visual medical information includes medical images acquired in a space of a certain dimension.

54. The medium according to claim 53, wherein the certain dimension of the space includes at least one of two-dimensions and three-dimensions.

55. The medium according to claim 41, wherein said fusing combines different types of the medically-related information in different modalities.

56. The medium according to claim 41, wherein said fusing combines different types of the medically-related information across different levels of the hierarchy.

57. The medium according to claim 41, wherein the medical decision is a diagnostic decision.

58. The medium according to claim 41, the instructions, when accessed, further enable navigating through information contained in the at least one matrix of diagnostic information.

59. The medium according to claim 41, the instructions, when accessed, further enable generating a report based on the medical decision.

60. The medium according to claim 59, wherein the report reporting the medical decision includes a link connecting the medical decision to diagnostic information represented in the at least one matrix and based on which the medical decision is made.

61. A method implemented on at least one machine each of which has at least one processor, storage, and communication platform for computer aided medical diagnosis, comprising:
obtaining, automatically via a search engine, medically-related information from different sources based on identifying information obtained from a user;
automatically forming, via a dynamic diagnostic decision matrix platform, a plurality of hierarchically arranged matrices of diagnostic information in a hierarchy, where a matrix at each level in the hierarchy is an assembly of organized medically-related information and generated by dynamically fusing different types of medically-related information from lower levels of the hierarchy, and each node in the hierarchy embeds a tool that can be activated when the diagnostic information is displayed;
modifying, via the dynamic diagnostic decision matrix platform, diagnostic information stored in at least one of the plurality of hierarchically arranged matrices;
updating, via the dynamic diagnostic decision matrix platform, the at least one hierarchically arranged matrix based on the modified diagnostic information stored therein to form updated hierarchically arranged matrices; and
computing, via the machine processor, a medical decision based on the updated hierarchically arranged matrices of diagnostic information, wherein
diagnostic information at any node of any level in the hierarchy is accessible and can be manipulated by the user interactively based on a data manipulation tool embedded with the diagnostic information,
diagnostic information at a level of the hierarchy can be dynamically fused with that at a same or a different level of the hierarchy based on a tool embedded with the diagnostic information, and
a result of the fusing is propagated within the hierarchy.

* * * * *